(12) United States Patent
Freeman et al.

(10) Patent No.: US 7,535,007 B1
(45) Date of Patent: May 19, 2009

(54) MULTIPLE CHAMBER DUAL CHANNEL INFRARED GAS DETECTION SYSTEM

(75) Inventors: Michael J. Freeman, Northville, MI (US); Steven Gautieri, Gladstone, MO (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 12/037,581

(22) Filed: Feb. 26, 2008

(51) Int. Cl.
*G01N 21/00* (2006.01)
(52) U.S. Cl. .................................................. 250/343
(58) Field of Classification Search ............ 250/339.13, 250/343
See application file for complete search history.

(56) References Cited

U.S. PATENT DOCUMENTS

| | | | | |
|---|---|---|---|---|
| 4,742,229 | A | * | 5/1988 | Weinel ........................ 250/343 |
| 5,146,283 | A | * | 9/1992 | Parnoff et al. ................ 356/246 |
| 2003/0177814 | A1 | * | 9/2003 | Weckstrom et al. ........ 73/25.01 |
| 2005/0224715 | A1 | * | 10/2005 | Devine ...................... 250/338.1 |
| 2006/0263256 | A1 | * | 11/2006 | Koshel et al. ................. 422/83 |
| 2008/0035848 | A1 | * | 2/2008 | Wong ......................... 250/345 |

OTHER PUBLICATIONS

PerkinElmer Optoelectronics Datasheet, Dual Thermopile Sensor TPS 2534 with 8.4 and 10.4 Filters, Dec. 4, 2007.
Honeywell Manning AirScan iR Datasheet, Sep. 2006.
Honeywell Manning AirScan iR Carbon Dioxide Datasheet, Jul. 2007.

* cited by examiner

*Primary Examiner*—David P Porta
*Assistant Examiner*—Marcus H Taningco
(74) *Attorney, Agent, or Firm*—Husch Blackwell Sanders Welsh & Katz

(57) ABSTRACT

A gas sensor usable in harsh environments includes a multiple chamber radiant energy transmission path which extends between a multi-channel emitter and a multi-channel detector. Chamber length and gas selection are establishable using a movable element with an aperture. The element is located between the emitter and the detector on the transmission path. Radiant energy from the emitter is reflected between the emitter and the element, prior to passing through the element to impinge on the detector.

19 Claims, 5 Drawing Sheets

MULTIPLE CHAMBER DUAL CHANNEL INFRARED GAS DETECTION SYSTEM

FIELD

The invention pertains to gas sensors. More particularly, the invention pertains to infrared, absorption-type gas sensors.

BACKGROUND

Commercial meat processing facilities often incorporate continuous product-flow blast freezers. Such freezers can incorporate a variety of different types of commercially available refrigerants such as $CO_2$, R22, R404, R507, R134A as well as ammonia.

Environments such as blast freezers where the ambient temperature is below −50° F. for several hours, and then, changes to 120° F. over a period of minutes, impose thermal shocks on gas sensors utilized to sense leaks in the refrigerant system. It is necessary during the warm-up and cool-down phase of a blast freezer to continuously determine if any refrigerant leaks are present.

There is a continuing need to monitor the ambient atmospheres of such freezers in real-time for refrigerant leaks. Preferably such sensors would be usable with more than one refrigerant gas, and, resistant to the thermal shocks of such freezers.

DETAILED DESCRIPTION

Figure 1:
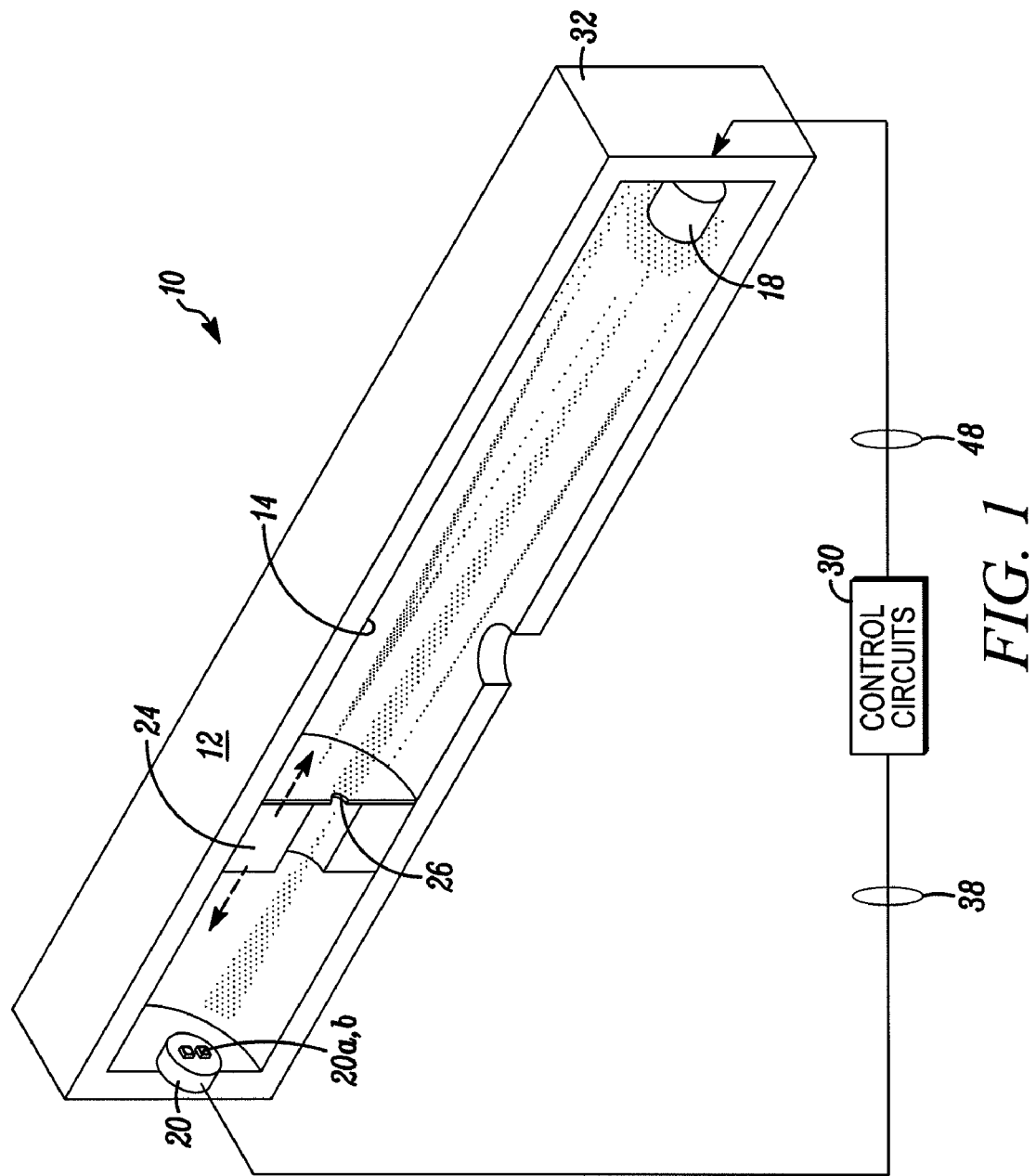
FIG. 1 is a diagram of a sensor in accordance with the invention.

While embodiments of this invention can take many different forms, specific embodiments thereof are shown in the drawings and will be described herein in detail with the understanding that the present disclosure is to be considered as an exemplification of the principles of the invention, as well as the best mode of practicing same, and is not intended to limit the invention to the specific embodiment illustrated.

Embodiments of the present invention relate to detecting the level of specific ambient gaseous molecules by infrared absorption spectrometry. IR "infrared" gas sensors in accordance with the invention sense gases in extreme environments where the prior art has limitations.

Embodiments of the present invention fill the voids of prior art and in current existing IR gas sensors and sense gas accurately during extreme thermal shock conditions. Another advantage of the present invention is the ability of the IR sensor to detect a multitude of gasses utilizing the same fixture or chamber and electronics.

In refrigerated environments, various refrigerants can be used depending on the customer's preference. Embodiments of the invention can be easily adapted to the specific analyte in use as a refrigerant.

Embodiments of the invention reduce the actual physical length of the chamber or "bench" where the sample volume permeates through for analysis. Several reflections from an IR source bounce from spaced apart ends where the detector and source are located providing an effective linear path length for IR absorption that is greater than the actual physical length of the chamber. This reduces the physical size and reduces material costs.

Sensors in accordance with the invention are preferably constructed of a rectangular block of aluminum with an internal hollowed out cylindrical polished chamber. A source and a dual-band detector are attached to each respective opened end of the chamber. Polished aluminum heat sinks carry the source and detector and simultaneously act as reflectors.

The detector can be implemented as a thermopile that reacts to temperature changes or incident IR energy differences from the source. As the analyte gas begins to permeate within the chamber or path from the source to the detector, IR energy is absorbed by the gas. Therefore, the detector receives less incident IR energy. This reduction in energy is translated into the number of molecules present in the chamber thereby sending a signal to associated control circuits for interpretation or ppm readings.

In the extreme environments where large temperature changes occur in a relatively short time, the heat sink/reflector provides thermal mass to the detector negating the effect of temperature transients that adversely affect the detector's performance during the abrupt fluctuations. The heat sink/reflector located on the source, also act as a means to cool the source during the off times increasing the signal to noise ratio between pulses. This improves sensor performance and allows for lower gas concentration readings.

The heat sinks also serve as reflectors on the ends of the chamber. As IR energy is irradiated by the source toward the detector, the reflector encompassing the detector sends back the energy to the source end. This energy is then reflected back to the detector by the reflector encompassing the source. This reflection process completes several iterations thereby increasing the number of molecules the IR energy can be absorbed in. This gives an increased overall effective path length that would normally not be available on a straight path chamber without reflectors on either end. This method allows for decreased chamber size and increased sensitivity.

Metal chamber designs which embody the invention provide stability over temperature changes, eliminate long-term mechanical alignment issues, provide electrical shielding, and particulate barriers. In addition to the heat sink/reflectors, the chamber can include a sliding aperture. The aperture location varies for each respective gas of interest by "tuning" the chamber for that specific gas. This sliding aperture is fixed by a fastener once the particular gas is selected for detection by the sensor.

The aperture enables IR from the source to be concentrated on the detector filter area with less phase cancellation, improves sensitivity, allows for smaller chamber sizes, limits the angle of incidence on the optical filters, and can improve absorption ratios by on the order of 30-40%. Advantageously, the multiple application of components provides simple, low-cost solutions to implementing sensors that can operate effectively and reliably in extreme environments. In addition, one chamber design can be utilized for a multitude of gasses reducing costs, inventory, and providing a common platform for ease of service/manufacturing.

In another aspect of the invention, the end caps of the sensor can be attached to the housing thereof and silver sintered metal disks can be provided to act as a diffusion barrier. This configuration enables the analyte to enter the chamber while excluding particulate contamination that could eventually block the source and optical filters. Those of skill in the art will understand that both linear and circular reflecting chambers come within the spirit and scope of the invention.

The source is preferable formed of a very thin low-mass flat or planar type filament encompassed by a cylindrical can. The can carries a CaFl window through which the IR emissions pass through before exiting from the can to the inside of the chamber.

The CaFl window reduces emissions or long wave energy above 11 microns to reduce the out of band energy for a better signal to noise ratio at the detector. This type of filter is used on refrigerants and ammonia detectors. Alternately, a Sapphire window can be provided where the gas of interest to be sensed is $CO_2$. In this configuration, the same source can be used.

The source is preferably pulsed or cycled once every two seconds. The ultra low-mass filament allows the source to heat up and cool down quickly. This facilitates accurate detection since the black body curve between pulses will tend to shift less on the pulse cycle.

The heat sink and reflector combination on the source end of the chamber serves several purposes. As a heat sink, just after the source turns off, residual energy on the metal can is quickly dissipated in the heat sink. Otherwise a small glow of the can would reduce signal to noise ratio just after the source shuts off.

The reflectors on both the aperture and source send IR energy back and fourth several times before the energy exits the aperture when used. If the aperture is not used, the energy bounces back and fourth from the detector reflector and source reflector. This multiple path bounce of energy increases the molecules of absorption or energy in the target gas sometimes referred to an analyte. The more energy that is absorbed in the target gas, the lower ppm detection level capabilities can exist or sensitivity.

The heat sink on the source end also helps reduce temperature swings. This provides the source with a thermal mass when the ambient temperature changes abruptly inside blast freezers during wash down when extreme temperature changes take place in a short period of time.

The heat sink and reflector on the detector also serve several purposes. The detector reacts to temperature changes as the source turns on and off. The detector is preferably a dual band thermopile with two filter windows. Incident radiant energy which passes through one filter can be used as a reference signal or channel. Radiant energy which passes through the other filter then corresponds to a target gas channel. Both channels are preferably compared to an archival signal when target gas is present. Use of a reference eliminates common mode changes in the environment and particulate contamination (micro sized) that could over years of use be masked out.

When the ambient temperature changes abruptly, the heat sink surrounding the detector provides thermal mass reducing the wide temperature swings. Since the detector reacts to temp changes, this swing could be mistaken as signal or increased noise on the output. The heat sink acts as a reflector as well for applications that do not use the aperture. IR energy is sent back to the source reflector and so on as described above.

The aperture acts as a reflector, optical concentrator, and incident angle control device. In applications where detection of low concentrations of a gas is required, a sliding aperture is useful for increasing the sensitivity of the sensor.

The angle of incidence (AOI) is important to the optical filters located on the thermopile. The filters are preferably band pass filters for wavelengths outside the target gas absorption band (the reference channel) and wavelengths within the absorption band (the target channel). The AOI is preferably less than 30 degrees. The center wavelengths shift proportionally to the AOI.

It is necessary to limit the AOI without degrading the energy from the source. Reducing energy from the source would decrease signal to noise ratio. Therefore, the aperture element has a small hole that results in multiple bounce energy between the source reflector and aperture reflector.

Eventually the IR energy for some path lengths that require multiple bounces exits through the small hole and is directed to the detector. Different distances from the source produce varying results on the constructive and destructive path length bounces within the chamber.

There is a distance with a standard deviation associated with the target wave length that has a small variance. The AOI on the detector can be varied by hole size and distance from the detector.

Since the distance from the source and aperture are a multiple of the target wave lengths, the AOI can be determined first. Then small changes can be made to the aperture to source distance to find the optimum point to obtain the best response to target gas. This is basic calibration can be made during manufacture and would never change throughout the sensor life.

FIG. 1 illustrates a sensor 10 in accordance with the present invention. Sensor 10 includes elongated, hollow metallic reflective housing 12. Housing 12 could be implemented for example with aluminum or other reflective metals or materials. An internal hollow, channel, or cavity 14 defines a transit path for radiant energy projected along and reflected within cavity 14.

One end of the housing 12 carries a source generally indicated at 18. Source 18 could be implemented with an emitter commercially available from Ion Optics. Emitted wavelengths are selected by using a filter. One wavelength band can be passed using a Sapphire window that produces a band on the order of 4-4.5 µm, usable for sensing $CO_2$. A second wavelength band on the order of 8-9 µm, usable for sensing refrigerants such as R404, 507, R22 and R134A can be passed using a CaFl window. Ammonia can be sensed using a BaFl window which passes a wavelength band on the order of 10-11 µm. Other sources of infrared energy come within the spirit and scope of the present invention.

Housing 12 also carries a dual channel detector 20 which could for example be implemented with a PerkinElmer Dual Thermopile No. TPS 2534. It will also be understood that other detectors come within the spirit and scope of the present invention.

Radiation of a selected wavelength emitted by a source 18 is reflected within cavity 14 along the sidewalls thereof as well as off of a moveable aperture insert, or element, indicated generally at 24. The element 24 includes a plurality of polished surfaces and fills the cavity 14 with the exception of aperture of 26 formed therein.

Element 24 can be located axially along the channel 14 for purposes of selecting a gas to be sensed. Reflected infrared radiant energy from source 18 passes through aperture 26 and impinges upon dual channel detector 20.

Filters 20a, 20b define a reference band and target gas band each of which is independently sensed at the detector 20. Reference and target gas signals are coupled to control circuits 30 for analysis. Control circuits 30 also are coupled to the source 18 and provide pulsed control signals thereto for purposes of generating infrared signals of the selected wavelength.

Both source 18 and detector 20 preferably surrounded, or encapsulated, by heat sinks, for example representative heat sink 32, illustrated in FIG. 1 adjacent to source 18. Such heat sinks protect the source 18 and the detector 20 from extreme intermittent temperature gradients found in flash freezers when such are being cycled between freezing temperatures and sterilization temperatures.

Figure 1A:
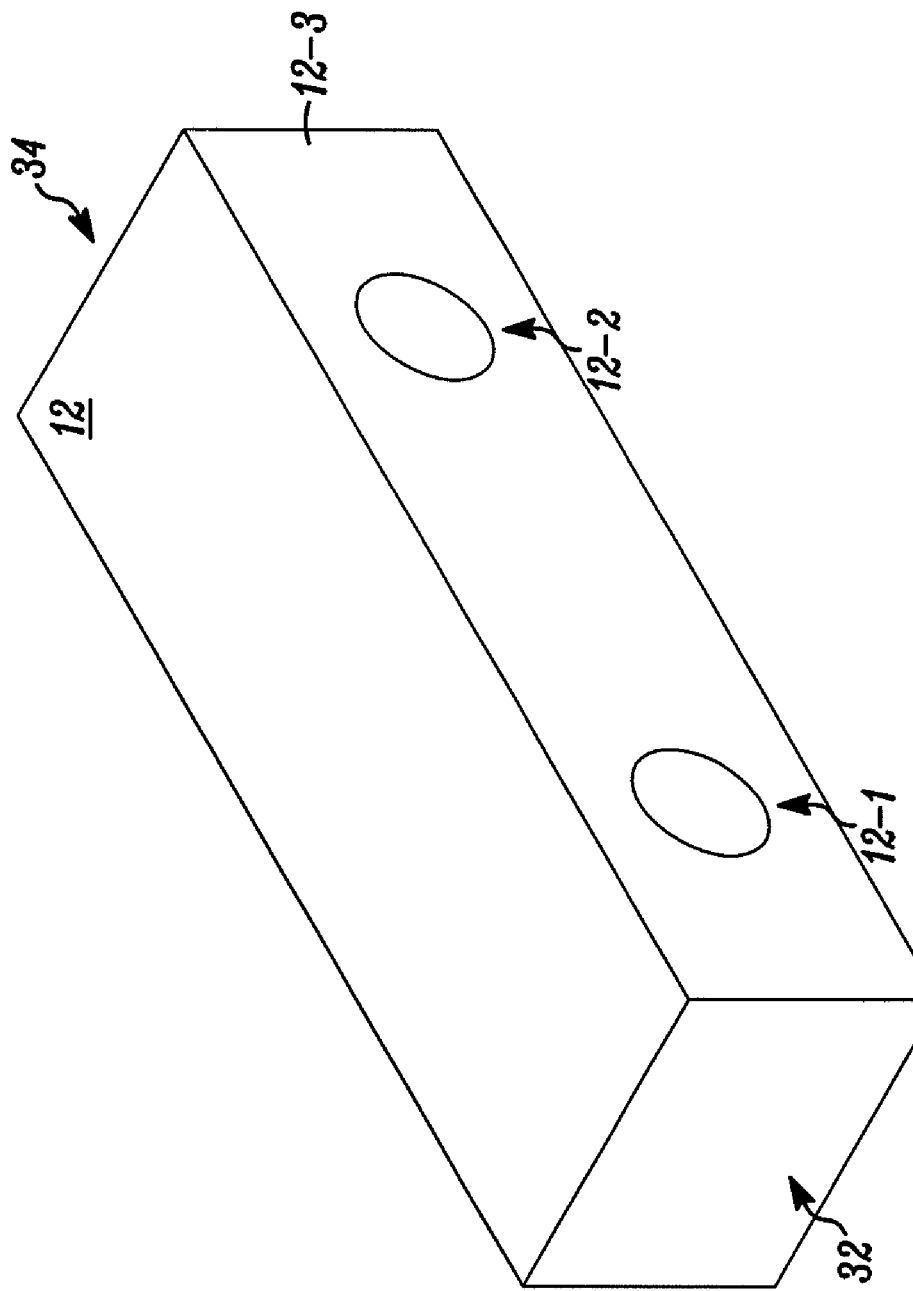
FIG. 1A illustrates additional aspects of the sensor as in FIG. 1.

FIG. 1A illustrates exemplary diffusion based inflow/outflow ports 12-1, -2 located on a side wall 12-3 of housing 12. The ports 12-1, -2 extend through the wall 12-3 of housing 12 to the internal radiant energy transit channel or cavity 14.

Each of the ports 12-1, 12-2 is preferably tapered, for example, having an exterior diameter on the order of ¾" and an interior diameter on the order of ¼". Ports 12-1, -2 can be filled with tapered, sintered metal plugs which permit diffusion based gas flow into and out of the chamber 14. Those of skill will understand that the above described configuration is exemplary only and that variations thereof come within the spirit and scope of the present invention.

Figure 2:
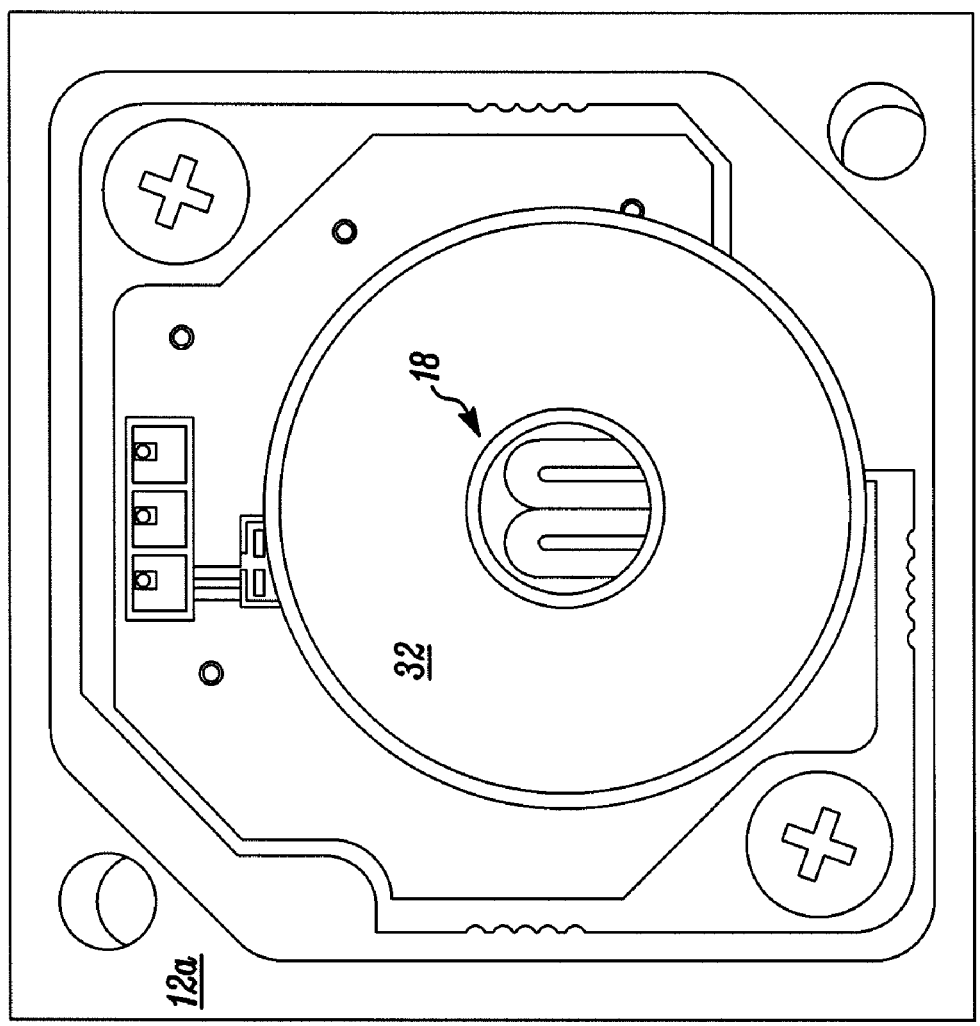
FIG. 2 is a view of a dual channel source and end cap usable with the sensor of FIG. 1.

FIG. 2 illustrates additional details of the source and heat sink combination 18, 32. As illustrated in FIG. 2 a dual wavelength source 18 can be substantially surrounded by a cylindrical heat sink 32. Those elements can also be carried on an end cap 12a of the housing 12.

Figure 3:
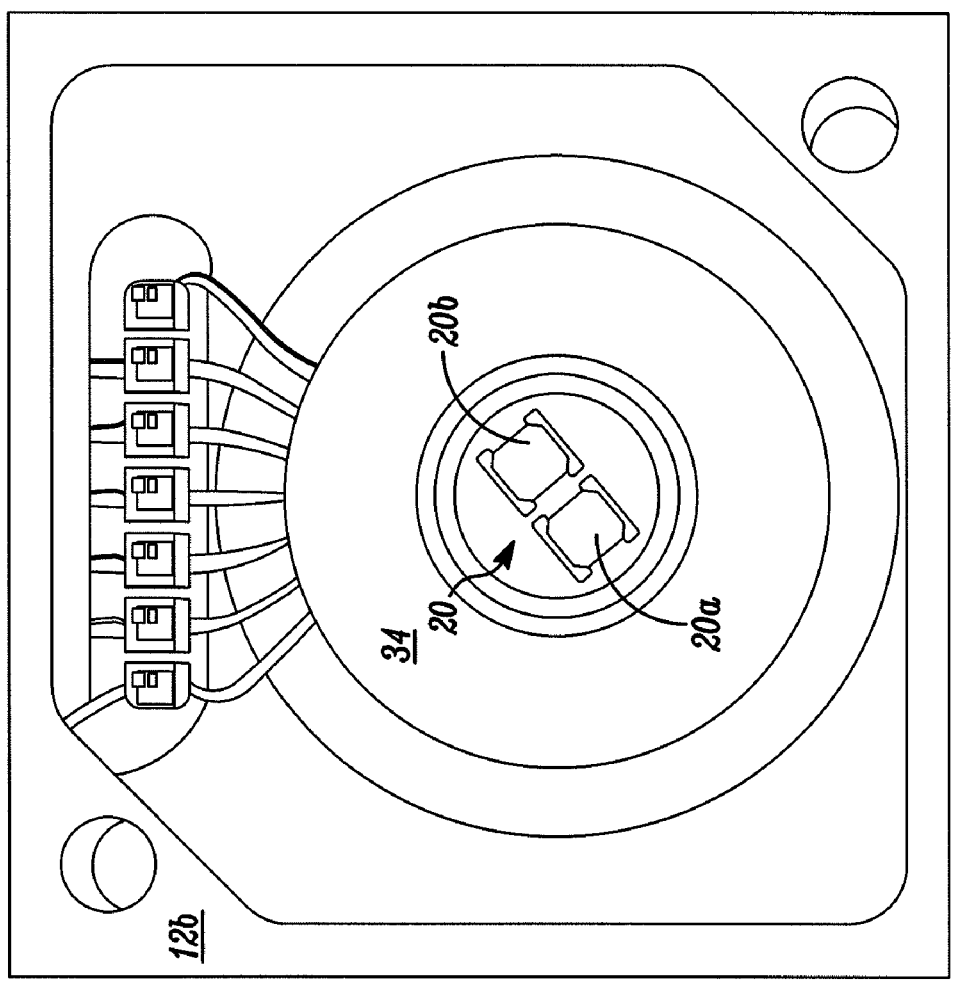
FIG. 3 is a view of a dual channel detector usable with the sensor of FIG. 1.

FIG. 3 illustrates additional details of the detector 20 and filters 20a, b which are surrounded by a cylindrical heat sink 34. The assembly of the detector 20 and heat sink 34 can be carried on an end cap 12b of the housing 12.

Figure 4:
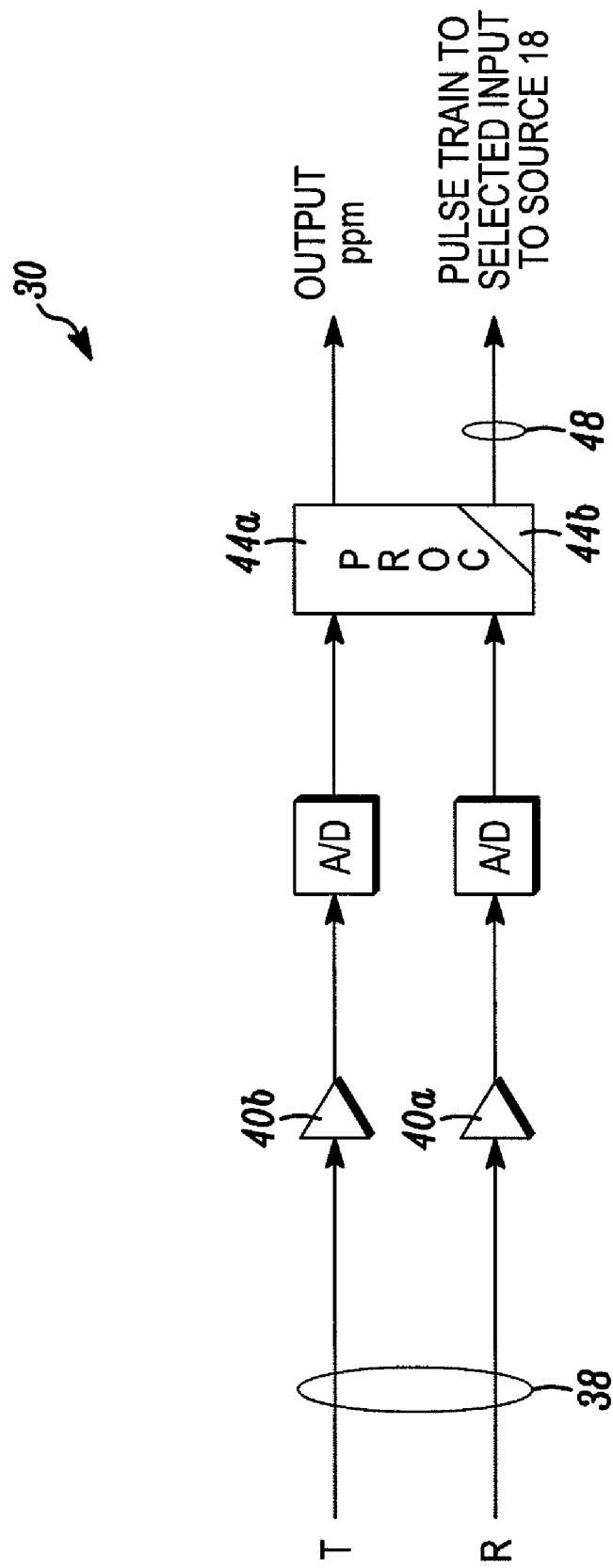
FIG. 4 is a block diagram of control circuits for the sensor of FIG. 1.

FIG. 4 illustrates additional aspects of control circuits 30. Control circuits 30 receive reference signals R and target signals T from detector 20 via wiring 38. Those signals can be amplified in amplifiers 40a and 40b. Amplified target and reference signals can be coupled to analog to digital converters 42a, b. Digital outputs can be coupled to a programmable processor 44a which operates under the control of software 44b.

Processor 44a can compare received and processed target signals to a pre-stored gas characterization curve to establish concentration of a target gas in parts per million. Exemplary ranges include a lower range of 0 parts per million and an upper range of 1,000 parts per million.

Those of skill in the art will recognize that a variety of processing of target and reference signals can be carried out without departing from the spirit and scope of the present invention. Processor 44a can also generate the above-noted pulse train of activation signals which can be coupled via wiring 48 to the source 18 to produce pulses of radiant energy at the selected wavelength.

From the foregoing, it will be observed that numerous variations and modifications may be effected without departing from the spirit and scope of the invention. It is to be understood that no limitation with respect to the specific apparatus illustrated herein is intended or should be inferred. It is, of course, intended to cover by the appended claims all such modifications as fall within the scope of the claims.

The invention claimed is:

1. A gas sensor comprising:
an elongated hollow housing which defines an internal, bounded transit path and which carries an infrared emitter and a displaced detector; and
a positionable aperture element on the path between the emitter and detector, location of the aperture element on the path is in accordance with a predetermined gas to be sensed.

2. A sensor as in claim 1 where the emitter is adjacent to a reflective heat sink.

3. A sensor as in claim 2 where the detector is adjacent to a reflective heat sink.

4. A sensor as in claim 3 where the aperture element carries a reflective surface which reflects radiant energy toward the emitter.

5. A sensor as in claim 4 where radiant energy from the emitter is reflected more than once between the aperture element, and, the emitter.

6. A sensor as in claim 5 where the radiant energy is reflected multiple times between the aperture element and the emitter before passing through the aperture of the element.

7. A sensor as in claim 6 where the detector and the aperture of the element are located on a common center line spaced apart from one another.

8. A sensor as in claim 7 which includes control circuits coupled to the emitter and the detector where the control circuits intermittently energize the emitter and receive intermittent signals from the detector.

9. A sensor as in claim 8 where the control circuits store at last one gas absorption profile.

10. A sensor as in claim 9 which includes a dual channel detector which emits first and second signals which are coupled to the control circuits.

11. A sensor as in claim 10 where the emitter comprises a dual channel emitter of first and second wavelengths.

12. A sensor as in claim 11 where first and second wavelength specifying inputs of the emitter are coupled to the control circuits.

13. A sensor as in claim 9 where heat sinks are carried adjacent to each of the emitter and detector.

14. A sensor as in claim 13 where diffusion barriers are carried adjacent to each of the emitter and detector.

15. A sensor as in claim 14 wherein the barriers comprise sintered metal.

16. A sensor as in claim 13 where the emitter emits at least one beam of radiant energy having a wavelength absorbed by at least one of airborne ammonia, carbon monoxide or carbon dioxide.

17. A sensor as in claim 1 wherein the hollow housing is one of substantially linear, or, curved.

18. A sensor comprising:
an elongated hollow housing which defines an internal, bounded, reflective transit path, the housing carries an infrared emitter and a displaced detector;
first and second heat sink reflective elements carried by the housing, spaced apart from one another, the elements close the transit path and encapsulate the emitter and the detector; and
which includes a positionable aperture element on the path between the emitter and detector, location of the aperture element on the path is in accordance with a predetermined gas to be sensed.

19. A sensor as in claim 18 where radiant energy from the emitter is reflected more than once between the aperture element, and, the emitter.

* * * * *